United States Patent [19]

Smith

[11] Patent Number: 5,238,924
[45] Date of Patent: Aug. 24, 1993

[54] TREATMENT OF RENAL DISEASES WITH ACE INHIBITORS

[75] Inventor: Ronald D. Smith, Worchester, Pa.

[73] Assignees: Merck & Co., Inc., Rahway, N.J.; Brigham & Women's Hospital, Boston, Mass.

[21] Appl. No.: 721,790

[22] Filed: Nov. 13, 1991

Related U.S. Application Data

[63] Continuation of Ser. No. 350,988, May 12, 1989, abandoned, which is a continuation of Ser. No. 170,220, Mar. 4, 1988, abandoned, which is a continuation of Ser. No. 855,977, Apr. 25, 1986, abandoned, which is a continuation-in-part of Ser. No. 723,989, Apr. 16, 1985, which is a continuation-in-part of Ser. No. 606,725, May 3, 1984, abandoned.

[51] Int. Cl.$^5$ .................. A61K 37/02; C07K 5/06
[52] U.S. Cl. ................................................ 514/19
[58] Field of Search ...................................... 514/19

[56] References Cited

PUBLICATIONS

S. Rasmussen et al., Scand J. Urol Nephrol, 17, 209–212 (1983).

Primary Examiner—Lester L. Lee
Attorney, Agent, or Firm—William H. Nicholson; Joseph F. DiPrima

[57] ABSTRACT

There is disclosed the use of angiotensin converting enzyme (ACE) inhibitors to alter the progression of renal diseases by affecting intraglomerular hemodynamics and proteinuria; i.e., affecting blood pressure within the functioning, filtering tissue of the kidney and the quantity of albumin in the urine.

20 Claims, No Drawings

TREATMENT OF RENAL DISEASES WITH ACE INHIBITORS

This is a continuation of application Ser. No. 350,988, filed May 12, 1989, now abandoned, which is a continuation of Ser. No. 170,220, filed March 4, 1988, now abandoned, which is a continuation of Ser. No. 855,977, filed Apr. 25, 1986, now abandoned, which is a continuation-in-part of application Ser. No. 723,989, filed Apr. 16, 1985, now abandoned, which is a continuation-in-part of application Ser. No. 606,725, filed May 3, 1984, now abandoned.

BACKGROUND OF THE INVENTION

The efficacy of angiotensin converting enzyme (ACE) inhibitors in the treatment of hypertension and congestive heart failure is known and has been amply demonstrated [U.S. Pat. No. 4,374,829, A. A. Patchett, et al., *Nature*, 288, 280-283 (1980); D. M. Gross, et al., *J. Pharm. and Expt. Ther.*, 216, 552-557 (1981)]. The use of such ACE inhibitors indicates the positive effects of control of Angiotensin II (A II) levels in a variety of renal disease states [C. D. Smith, et al., *Arthritis and Rheumatism* (1984)].

It has been generally known for some time that a renal factor is involved in some forms of hypertension, but only relatively recently have some of the complete relationships in the "renin angiotensin system" been elucidated. In addition to its direct vasopressor effects and its control of adrenal secretion of aldosterone, A II has a direct effect on glomerular size and basement membrane porosity. [D. P. Haley, et al., *Abstract of Proceedings of Amer. Soc. of Nepth;* 151A (1983); S. J. Hoorntje.]

Heretofore, clinical studies have been directed to the blockade of the renin angiotensin system in the systemic circulation to control hypertension and congestive heart failure. Specific renin angiotensin systems have been observed to be present within the cells of specific organ systems such as, for example, the kidney, heart, brain, and blood vessels. M. R. Celio, et al. [*Proc. Natl. Acad. Sci. USA*, 78, 3897 (1981) and *Histochemistry*, 72, 1 (1981)] have identified in rats the specific glomerular sites of A II production from angiotensin I (A I) and have demonstrated its subsequent blockage by the ACE inhibitor compound, enalapril.

It has also been found that infusions of A II onto preparations of renal glomeruli produced shrinking of the glomerulus and smudging of the foot processes which is attendant with the development of proteinuria. [S. J. Hoorntje, supra]. Upon elimination of the infused A II, these actute, transitory changes disappear and proteinuria, glomerular volume, and foot processes configurations then return to normal. Although it has not yet been established, it appears that glomerular sclerosis plays a major role in progressive degradation of renal function regardless of the original etiology of the kidney disease. Clinically, it has been postulated that control of proteinuria in renal disease would result in controlling the underlying renal pathology. [R. B. Miller, et al., *Amer. J. Med.,* 46, 919 (1969)].

It has also been known that hypertension can produce renal disease and that renal disease can produce hypertension [*Renal and Electrolyte Disorders,* 282, Ed by R. W. Schrier (1976)]. Although the control of hypertension through the use of ACE inhibitors has been established [M. Burnier, et al., *Amer. J. of Physiology,* 245, 203 (1983); H. R. Brunner, et al., *Am. Int. Med.,* 90, 19 (1979)] it has yet to be determined that subsequent development of renal diseases will be ablated or even blunted by these agents.

Diabetic nephropathy is also known to be associated with specific lesions in the kidney and eye, hypertension [D. Myers, et al, *Clin. Res.,* 27:316A, (1979)], and relative increases in circulating renin [W. A. Hsueh, et al, *J. Clin. Endo. Metab.,* 51:535, (1980)]. It has been postulated that the vascular lesions are related to the vasculotoxic effects of A II. Therefore, the inhibition of A II would be expected to have a positive effect on the course of the renal disease.

It has been demonstrated that administration of the ACE inhibitor, enalapril, effectively blocks the pressor response to exogenous administered A I and significantly suppresses the activity of circulating converting enzyme for periods of up to about 24 hours. [D. M. Gross, et al., *J. Pharm. and Expt. Ther.,* 216, 552-557 (1981)]. Specific localization of enalapril in the kidney has been demonstrated as has its specific effect on the local production of A II within the glomerulus. As reported by D. E. Hricik, et al. [*N. E. J. Med.,* 308, 373 (1983)], one might assume that in the A II dependent arterial stenotic kidney, renal insufficiency could occur upon administration of enalapril. However, it has been demonstrated that administration of enalapril in renin dependent states, such as renal vascular hypertension, results in virtual total control of blood pressure [S. Franklin, *Am. J. Med.,* 79, 14 (1985)].

As reported by S. Anderson et al., [*J. Clin. Investigation,* in press (1986)], protection against the progression of renal disease in hypertensive rats was accomplished with the addition of enalapril, but not with the addition of standard antihypertensive medication (reserpine, hydralazine, and hydrochlorothiazide). Although both therapies controlled blood pressure compared to control animals, intraglomerular pressure ($\Delta P$), basement membrane characteristics ($K_f$), and resulting proteinuria and glomerulosclerosis were controlled with ACE inhibition therapy, but not with the standard triple therapy. The degree of proteinuria and glomerulosclerosis in the standard triple therapy was similar to untreated animals. Thus, it is demonstrated that control of systemic blood pressure alone does not positively effect the progression of renal disease.

SUMMARY OF THE INVENTION

It has now been found that administration of angiotensin converting enzyme (ACE) inhibitors alters renal hemodynamics in that ACE inhibitors have a positive effect on progressive renal failure which is manifested by such deficiencies as intraglomerular hypertension, progressive glomerular sclerosis, progressive proteinuria, azotemia, regardless of the etiology of the initial renal insult such as glomerulo nephritis, diabetic nephropathy, nephrotic syndrome, and the like.

Representative of the angiotensin converting enzyme (ACE) inhibitors that have been found to be useful in altering the progression of renal diseases by affecting intraglomerular hemodynamics and proteinuria are such ACE inhibitors as carboxyalkyl dipeptide derivatives; captopril [1-(3-mercapto-2-methyl-1-oxopropyl)-L-proline]; 2-[N-(S)-1-ethoxycarbonyl-3-phenylpropyl)-S-alanyl]-cis,endo-2-aza-bicyclo[3,3,0]-octane-3(S)-carboxylic acid; N-((S)-1-ethoxycarbonyl-3-phenylpropyl)-L-alanyl-N-(2-indanyl)glycine; 1-(N-[(S)-1-ethoxycarbonyl-3-phenylpropyl]-L-alanyl)-cis,- syn-octahydro-(H-indole-2-S)-carboxylic acid; 2-(N-[(S)-1-ethoxycarbonyl-3-phenylpropyl]-L-alanyl)-1,2,3,4-tetrahydroiso-isoquinoline-3(S)-carboxylic acid; and, 1-carboxymethyl-3(S)-(1(S)-ethoxycarbonyl-3-phenylpropylamino)-2,3,4,5-tetrahydro-1H[1]-benzazepine-2-one.

In particular, the class of carboxyalkyl dipeptide derivatives which have been found to have this positive effect on progressive renal failure are those disclosed in U.S. Pat. No. 4,374,829, which also discloses method for their preparation and which patent is incorporated herein by reference. Of the carboxyalkyl dipeptides disclosed in U.S. Pat. No. 4,374,829, those of particular interest in this invention are N-[1(S)-ethoxycarbonyl-3-phenylpropyl]-L-alanyl-L-proline, also known and referred to herein as enalapril; N-[1(S)-carboxy-3-phenylpropyl]-L-alanyl-L-proline, also known and referred to herein as enalapril diacid; and, N$\alpha$[1(S)-carboxy-3-phenylpropyl]-L-lysyl-L-proline, also known and referred to herein as lisinapril.

Thus, this invention is directed to the treatment of progressive renal failure which is manifested by such deficiencies as intraglomerular hypertension, progressive glomerular sclerosis, progressive proteinuria, azotemia, regardless of the etiology of the initial renal insult such as glomerulo nephritis, diabetic nephropathy, nephrotic syndrome, and the like, which treatment comprises administering to a person in need of such treatment a renal failure inhibiting amount of an angiotensin converting enzyme inhibitor compound which is a member selected from the group consisting of: carboxyalkyl dipeptide derivatives; 1-(3-mercapto-2-methyl-1-oxopropyl)-L-proline; 2-[N-(S)-1-ethoxycarbonyl-3-phenylpropyl)-S-alanyl]-cis,endo-2-azabicyclo[3,3,0]octane-3(S)-carboxylic acid; N-((S)-1-ethoxycarbonyl-3-phenylpropyl)-L-alanyl-N-(2-indanyl)-glycine; glycine; 1-(N-[(S)-1-ethoxycarbonyl-3-phenylpropyl]-L-alanyl)-cis,syn-octahydro-(H-indole-2-S)-carboxylic acid; 2-(N-[(S)-1-ethoxycarbonyl-3-phenylpropyl]-L-alanyl)-1,2,3,4-tetrahydroiso-isoquinoline-3(S)-carboxylic acid; and, 1-carboxymethyl-3(S)-(1(S)-ethoxycarbonyl-3-phenylpropylamino)-2,3,4,5-tetrahydro-1H[1]-benzazepine-2-one.

Preferably, the angiotensin converting enzyme inhibitor compound is a member selected from the group:

N-[1(S)-ethoxycarbonyl-3-phenylpropyl]-L-alanyl-L-proline;

N-[1(S)-carboxy-3-phenylpropyl]-L-alanyl-L-proline; or,

N$\alpha$[1(S)-carboxy-3-phenylpropyl]-L-lysyl-L-proline.

Pursuant to this invention, administration of one of these renal failure inhibiting compounds results in altering the progression of renal disease by affecting the intraglomerular hemodynamics and proteinuria; i.e., the blood pressure within the functioning, filtering tissue of the kidney and the quantity of albumin in the urine, to effectively treat such deficiencies as intraglomerular hypertension, progressive glomerular sclerosis, progressive proteinuria, azotemia regardless of the etiology of the initial renal insult such as glomerulo nephritis, diabetic nephropathy, nephrotic syndrome, and the like.

For use in treating progressive renal failure, an ACE inhibitor compound can be administered orally, transdermally, or parenterally; i.e., intravenously, interperitoneally, etc. and in any suitable dosage form. Thus, the compounds may be offered in a form (a) for oral administration; e.g., as tablets, in combination with other compounding ingredients customarily used such as talc, vegetable oils, polyols, benzyl alcohols, gums, gelatin, starches and other carriers; dissolved or dispersed or emulsified in a suitable liquid carrier; in capsules or encapsulated in a suitable encapsulating material; or (b) for parenteral administration; e.g., dissolved or dispersed in a suitable liquid carrier or emulsified.

The ratio of active compound to compounding ingredients; i.e., carrier, diluent, etc., will vary as the dosage form requires. Whatever dosage form is used, the amount of compound administered should be sufficient to effect (a) blood pressure control, (b) reduce proteinuria; and (c) reduce glomerular lesions. Generally, doses of the compounds of the invention can be administered in amounts of from about 0.1 mg to about 1 g and preferably from about 5 to about 500 mg per day. Dosage may be single or multiple depending on the daily total required and the unit dosage.

DETAILED DESCRIPTION OF THE INVENTION

The following example sets forth the best mode currently known for practicing the invention and is intended to be illustrative and not limitative of the invention.

EXAMPLE 1

Augmented glomerular capillary pressure ($P_{GC}$) and flow ($Q_A$) are associated with progressive glomerular injury in rats with reduced nephron number; i.e., the number of functioning units within the kidney. The role of these hemodynamic changes in remnant renal injury was evaluated by comparing male Munich-Wistar rats subjected to 85% oblation of renal mass; i.e., surgical removal of 85% of the kidney, and given either no treatment (C) or a compound of the invention; i.e., enalapril (E). Results obtained after 4 weeks showed that E controlled systemic blood pressure [awake systolic pressure (SBP) and mean arterial pressure under anesthia (AP)] and nearly normalized $P_{GC}$ while the supranormal single nephron glomerular filtration rate (SNGFR) and flow ($Q_A$) seen in remnant kidneys of rats given no treatment (C) were only modestly reduced. These results are set forth in Table I below wherein values are given as $\pm 1$ SE; i.e., standard error, and wherein n denotes the number of animals (rats) tested; ml/m denotes milliliters per minute; nl/m denotes nanoliters/per minute; mg/d denotes milligrams per day; and, GFR denotes glomerular filtration rate.

TABLE I

| Test Rats | SBP | AP | $PG_C$ | GFR (ml/m) | SNGFR (nl/m) | $Q_A$ (nl/m) |
|---|---|---|---|---|---|---|
| C (n = 6) | 169 ± 8 | 245 ± 5 | 68 ± 2 | 0.92 ± 0.05 | 102 ± 8 | 374 ± 28 |
| E (n = 6) | 115 ± 5* | 102 ± 2* | 34 ± 2* | 0.85 ± 0.05 | 84 ± 9 | 312 ± 41 |

*p < 0.01 E vs. C

After 8–9 weeks, similarly prepared C rats (no treatment) exhibited continued hypertension (SBP, 179±10; AP, 141±6 mmHg), developed proteinuria (70±10 mg/d) and extensive glomerular lesions (epithelial cell bleb, droplet formation; and, segmental sclerosis) whereas E treated rats (treated with enalapril) exhibited continued blood pressure control (SBP, 125±3; AP, 102±3 mmHg), developed significantly less proteinuria (18±2 mg/d), and markedly fewer glomerular lesions (21% treated vs. 6% non-treated).

The foregoing results indicate that control of glomerular hypertension by use of the ACE inhibitor compounds of the invention effectively limits glomerular injury in rats having renal ablation and that as a result of these glomerular hemodynamic changes, progressive renal injury is mediated when nephron number is reduced.

It also appears from the foregoing that a decrease in transmembrane selective permeability [$(K_f)$ or (LpA)] not only contributes to proteinuria, but also alters the passage of proteins into the mesangial cells with subsequent glomerular sclerosis.

EXAMPLE 2

Male Munich-Wister rats were studied 4-6 weeks after being injected with streptozotocin (60 mg/kg). The blood glucose (BG) level of the rats was maintained between 200-400 mg/d by daily injections of ultralente insulin. The rats were divided into two groups, one group receiving an additional treatment (group DM) and the other group receiving 15 mg/l of enalapril (E) in their drinking water (group DMX). Another group of age-matched normal rats were evaluated as the control group (group C). The results of these studies are set forth in Table II below wherein the results are given as ±1 SE and wherein MAP denotes mean arterial pressure; KW denotes kidney weight; and ΔP denotes the difference in pressure measured across the glomerular membrane.

TABLE II

| Test Rats Group | BG (mg/d) | MAP (mm Hg) | KW (g) | SNGFR (nl/m) | $Q_A$ (nl/m) | TP (mm Hg) |
|---|---|---|---|---|---|---|
| C (n = 7) | 87 ± 3 | 118 ± 3 | 1.1 ± 0.1 | 45 ± 4 | 154 ± 38 | 39 ± 1 |
| DM (n = 8) | 350 ± 11* | 115 ± 4 | 1.5 ± 0.1* | 52 ± 6* | 269 ± 26* | 52 ± 2* |
| DMX (n = 8) | 346 ± 14* | 98 ± 4** | 1.3 ± 0.1** | 72 ± 7* | 227 ± 14* | 37 ± 1 |

*$p < 0.05$ vs. C
**$p < 0.05$ vs. DM

The results shown in Table II above reveal that the DM group of rats had marked elevations in kidney weight (KW), single nephron glomerular filtration rate (SNGFR), augmented glomerular capillary flow ($Q_A$), and glomerular membrane pressure (ΔP). Despite similar increases in BG levels, the DMX group of rats exhibited normalization of ΔP as well as lesser elevations in SNGFR and $Q_A$, primarily as a result of lower MAP.

Additional rats divided into the same types of groups, i.e., groups C, DM and DMX, were maintained under similar conditions for a period of 6-8 months. Albuminurea (mg/24 h) for these groups of rats were found to be as follows:
Group C: 3±1
Group DM: 32±8
Group DMX: 4±1
($p < 0.05$ DM vs. C; $p < 0.05$ DMX vs. DM).

These results establish that intraglomerular hypertension and progressive proteinuria can be readily reversed in the initiation of diabetic glomerular disease by treatment with an angiotensin converting enzyme inhibitor compound of the invention.

What is claimed is:

1. A method of treating progressive renal failure which is manifested by such deficiences as intraglomerular hypertension, progressive glomerular sclerosis, progressive proteinuria, azotemia, regardless of the etiology of the initial renal insult which method comprises administering to a patient in need of such treatment a renal failure inhibiting amount of an angiotensin converting enzyme inhibitor carboxyalkyl dipeptide compound.

2. The method of claim 1 wherein said angiotensin converting enzyme inhibitor compound is a member selected from the group consisting of carboxyalkyl dipeptide derivatives;
   1-(3-mercapto-2-methyl-1-oxopropyl)-L-proline;
   2-[N-(S)-1-ethoxy-carbonyl-3-phenylpropyl)-S-alanyl]-cis,endo-2-aza-bicyclo[3,3,0]octane-3(S)-carboxylic acid;
   N-((S)-1-ethoxycarbonyl-3-phenylpropyl)-L-alanyl-N-(2-indanyl)-glycine;
   1-(N-[(S)-1-ethoxycarbonyl-3-phenylpropyl]-L-alanyl-cis,syn-octahydro-(H-indole-2-S)-carboxylic acid;
   2-(N-[(S)-1-ethoxycarbonyl-3-phenylpropyl]-L-alanyl)-1,2,3,4-tetrahydroiso-isoquinoline-3(S)-carboxylic acid; and,
   1-carboxymethyl-3(S)-(1(S)-ethoxycarbonyl-3-phenylpropylamino)-2,3,4,5-tetrahydro-1H[1]-benzazepine-2-one.

3. The method of claim 2 wherein said carboxyalkyl dipeptide derivatives are selected from the group consisting of:
   N-[1(S)-ethoxycarbonyl-3-phenylpropyl]-L-alanyl-L-proline;
   N-[1(S)-carboxy-3-phenylpropyl]-L-alanyl-L-proline; or,
   N-α-[1(S)-carboxy-3-phenylpropyl]-L-lysyl-L-proline.

4. A method of treating progressive renal failure which is manifested by such deficiencies as intraglomerular hypertension, progressive glomerular sclerosis, progressive proteinuria, azotemia, regardless of the etiology of the initial renal insult which method comprises administering to a person in need of such treatment a renal failure inhibiting amount of an angiotensin converting enzyme inhibitor compound which is a member selected from the group consisting of:
   N-[1(S)-ethoxycarbonyl-3-phenylpropyl]-L-alanyl-L-proline;
   N-[1(S)-carboxy-3-phenylpropyl]-L-alanyl-L-proline; or,
   Nα-[1(S)-carboxy-3-phenylpropyl]-L-lysyl-L-proline.

5. A method of treating progressive renal failure that comprises administering to a patient in need of such treatment a renal failure inhibiting amount of an angiotensin converting enzyme inhibitor compound.

6. The method of claim 5 wherein said angiotensin converting enzyme inhibitor compound is a member selected from the group consisting of carboxyalkyl dipeptide derivatives;

1-(3-mercapto-2-methyl-1-oxopropyl)-L-proline;

2-[N-(S)-1-ethoxy-carbonyl-3-phenylpropyl)-S-alanyl]-cis,endo-2-aza-bicyclo[3,3,0]octane-3(S)-carboxylic acid; N-((S)-1-ethoxycarbonyl-3-phenylpropyl)-L-alanyl-N-(2-indanyl)-glycine;

1-(N-[(S)-1-ethoxycarbonyl-3-phenylpropyl]-L-alanyl-cis,syn-octahydro-(H-indole-2-S)-carboxylic acid;

2-(N-[(S)-1-ethoxy- carbonyl-3-phenylpropyl]-L-alanyl)1,2,3,4-tetrahydroiso-isoquinoline-3(S)-carboxylic acid; and, 1-carboxymethyl-3(S)- (1(S)-ethoxycarbonyl-3-phenylpropylamino)-2,3,4,5-tetrahydro-1H [1]-benzazepine-2-one.

7. The method of claim 6 wherein said carboxyalkyl dipeptide derivatives are selected from the group consisting of:

N-[1(S)-ethoxycarbonyl-3-phenylpropyl]-L-alanyl-L-proline;

N-[1(S)-carboxy-3-phenylpropyl]-L-alanyl-L-proline; or,

N-α-[1(S)-carboxy-3-phenylpropyl]-L-lysyl-L-proline.

8. A method of treating progressive renal failure that comprises administering to a person in need of such treatment a renal failure inhibiting amount of an angiotensin converting enzyme inhibitor compound which is a member selected from the group consisting of:

N-[1(S)-ethoxycarbonyl-3-phenylpropyl]-L-alanyl-L-proline;

N-[1(S)-carboxy-3-phenylpropyl]-L-alanyl-L-proline; or,

N-α-[1(S)-carboxy-3-phenylpropyl]-L-lysyl-L-proline.

9. The method of claim 1 wherein the progressive renal failure is caused by glomerulonephritis.

10. The method of claim 1 wherein the progressive renal failure is caused by diabetic nephropathy.

11. The method of claim 1 wherein the progressive renal failure is caused by normotensive diabetes.

12. The method of claim 4 wherein the progressive renal failure is caused by glomerulonephritis.

13. The method of claim 4 wherein the progressive renal failure is caused by diabetic nephropathy.

14. The method of claim 4 wherein the progressive renal failure is caused by normotensive diabetes.

15. The method of claim 5 wherein the progressive renal failure is caused by glomerulonephritis.

16. The method of claim 5 wherein the progressive renal failure is caused by diabetic nephropathy.

17. The method of claim 5 wherein the progressive renal failure is caused by normotensive diabetes.

18. The method of claim 8 wherein the progressive renal failure is caused by glomerulonephritis.

19. The method of claim 8 wherein the progressive renal failure is caused by diabetic nephropathy.

20. The method of claim 8 wherein the progressive renal failure is caused by normotensive diabetes.

* * * * *

UNITED STATES PATENT AND TRADEMARK OFFICE
CERTIFICATE OF CORRECTION

PATENT NO.   : 5,238,924
DATED        : August 24, 1993
INVENTOR(S)  : Ronald D. Smith and Barry M. Brenner It is certified that error appears in the above-identified patent and that said Letters Patent is hereby corrected as shown below:

On the title page, replace "Brigham & Women's Hospital," with --The Brigham and Women's Hospital, Inc.--.

Signed and Sealed this

Thirtieth Day of August, 1994

Attest:

BRUCE LEHMAN

Attesting Officer          Commissioner of Patents and Trademarks

UNITED STATES PATENT AND TRADEMARK OFFICE
CERTIFICATE OF CORRECTION

PATENT NO. : 5,238,924
DATED : August 24, 1993
INVENTOR(S) : Ronald D. Smith, et al It is certified that error appears in the above-indentified patent and that said Letters Patent is hereby corrected as shown below:

On title page, item [75] should read as follows:

-- Inventors: Ronald D. Smith, Worchester, PA
and Barry M. Brenner, Weston, MA

Signed and Sealed this

Eighteenth Day of October, 1994

*Attest:*

BRUCE LEHMAN

*Attesting Officer*   *Commissioner of Patents and Trademarks*